United States Patent [19]

Hoppe et al.

[11] Patent Number: 5,889,062

[45] Date of Patent: Mar. 30, 1999

[54] COMPOSITIONS AND METHODS FOR THE TREATMENT OF AGING SKIN

[75] Inventors: Udo Hoppe, Hamburg; Gerhard Sauermann, Wiemersdorf; Volker Schreiner; Klaus-Michael Steiger, both of Hamburg, all of Germany

[73] Assignee: Beiersdorf AG, Hamburg, Germany

[21] Appl. No.: 718,592

[22] PCT Filed: Mar. 24, 1995

[86] PCT No.: PCT/EP95/01117

§ 371 Date: Dec. 24, 1996

§ 102(e) Date: Dec. 24, 1996

[87] PCT Pub. No.: WO95/26181

PCT Pub. Date: Oct. 5, 1995

[30] Foreign Application Priority Data

Mar. 25, 1994 [DE] Germany ............... 44 10 238.0

[51] Int. Cl.$^6$ .................................. A61K 31/12

[52] U.S. Cl. ........................................ 514/690

[58] Field of Search ............................... 514/690

[56] References Cited

U.S. PATENT DOCUMENTS 3,629,409  12/1971  Gregory .................. 424/195
5,378,461   1/1995  Neigut ..................... 424/94.1

*Primary Examiner*—Leonard Schenkman
*Attorney, Agent, or Firm*—Sprung Kramer Schaefer & Briscoe

[57] ABSTRACT

Topical formulations having a content of one compound or several compounds from the group consisting of ubiquinones and derivatives thereof in combination with a content of one compound or several compounds from the group consisting of plastoquinones and derivatives thereof or formulations having a content of one compound or several compounds from the group consisting of plastoquinones and derivatives thereof.

6 Claims, No Drawings

COMPOSITIONS AND METHODS FOR THE TREATMENT OF AGING SKIN

The present invention relates to active compounds and formulations for care of aged skin and for prophylaxis and treatment of chronological aging of the skin which may additionally be intensified or accelerated by exogenous factors.

Chronological aging of the skin is caused, for example, by endogenous, genetically determined factors. In the epidermis and dermis, the following aging-related structural damage and dysfunctions, which can also fall under the term "senile xerosis", occur:

a) Dryness, roughness and the development of dryness wrinkles, b) itching and c) reduced re-oiling by sebaceous glands (for example after washing).

Exogenous factors, such as UV light and chemical noxae, may have a cumulative action and, for example, accelerate or supplement the endogenous aging processes. In the epidermis and dermis, for example, the following structural damage and dysfunctions in the skin, which go beyond the extent and quality of damage during chronological aging, occur in particular due to exogenous factors:

d) Visible dilation of vessels (couperosis);

e) flaccidity and development of folds;

f) local hyper- and hypopigmentation and defective pigmentation (for example senile keratosis) and g) increased susceptibility to mechanical stress (for example cracking).

The present invention particularly relates to products for care of skin aged in a natural manner, and for treatment of the secondary damage of aging caused by light, in particular the phenomena listed under a) to g).

Products for the care of aged skin are known per se. They comprise, for example, retinoids (vitamin A acid and/or derivatives thereof) or vitamin A and/or derivatives thereof. However, the extent of their action on structural damage is limited. Furthermore, during product development, there are considerable difficulties in stabilizing the active compounds adequately against oxidative decay. The use of products comprising vitamin A acid moreover often causes severe erythematous skin irritations. Retinoids can therefore be employed only in low concentrations.

Cosmetic formulations with coenzyme Q-10 which are suitable for treatment of skin diseases, for prophylaxis of dystrophic and dysmetabolic states of the skin and for use on chemical and physical respiratory damage or in cases of delayed respiration associated with age and wear are furthermore known from DE-A-33 09 850.

Japanese Laid-Open Specification 58,180,410 describes the suitability of coenzyme Q-10 for cosmetics. It is said to activate skin cell metabolism and suppress oxidation. As a result, coenzyme Q-10 has an important function in the prevention of skin damage due to UV radiation and the prevention of aging of the skin. Roughness of the skin of 20- to 40-year olds is improved by giving the skin moisture.

The object of the present invention was thus to discover ways of avoiding the disadvantages of the prior art. In particular, the action of eliminating the damage associated with endogenous, chronological and exogenous aging of the skin and prophylaxis should be permanent, lasting and without the risk of side effects.

These objects are achieved by the invention.

The invention relates to topical formulations having a content of one compound or several compounds from the group consisting of ubiquinones and derivatives thereof in combination with a content of one compound or several compounds from the group consisting of plastoquinones and derivatives thereof, or formulations having a content of one compound or more compounds from the group consisting of plastoquinones and derivatives thereof (as only one group of active compounds).

The topical formulations according to the invention can be cosmetic or dermatological formulations. They are preferably used, as are also the active compounds, for prophylaxis and/or treatment of aging of the skin of chronological and/or exogenous origin.

The invention also relates to the use of one compound or several compounds from the group consisting of ubiquinones and derivatives thereof in combination with one compound or several compounds from the group consisting of plastoquinones and derivatives thereof, or the use of one compound or several compounds from the group consisting of plastoquinones and derivatives thereof, in each case for prophylaxis and/or treatment of aging of the skin of chronological and/or exogenous origin.

"Ubiquinones" and "plastoguinones" here also mean "ubiquinones and derivatives thereof" and "plastoquinones and derivatives thereof".

It has been found, surprisingly, that ubiquinones and derivatives thereof and/or plastoquinones and derivatives thereof not only protect the skin from damage due to chronological aging of the skin, but in particular aging caused by light, but also bring about the repair of damage, which significantly remedies disadvantages of the prior art. This action of this group of substances on structural changes of aged skin is particularly advantageous.

During chronological aging of the skin, the following age-related structural damage and dysfunctions:

a) Dryness, roughness and development of skin wrinkles, b) itching c) reduced re-oiling by sebaceous glands (for example after washing) and the disturbances of senile xerosis, in particular those as described under a) to c), occur in particular.

During aging of the skin of exogenous origin, for example caused by UV light and chemical noxae, the following dysfunctions occur in particular:

d) Visible dilation of vessels (couperosis);

e) flaccidity and development of folds;

f) local hyper- and hypopigmentation and defective pigmentation (for example senile keratosis) and g) increased susceptibility to mechanical stress (for example cracking).

Ubiquinones are known from the literature (for example "Römpp Chemie Lexikon" [Römpp's Chemical Dictionary], Georg Thieme Verlag, Stuttgart, N.Y., 9th Edition, pages 4784–4785 or "The Merck Index", 11th Edition, Merck & Co., Inc. Rahway, N.Y., USA, Abstract 9751 (1989)). They are also called mitoquinones or coenzymes Q. The number of isoprene units in the side chain is stated with n in the designation coenzymes Q-n, wherein n is an integer. Preferred ubiquinones or coenzymes Q-n are those where n=0–12, particularly preferably n=1–12, and in particular n=6 to 10. The invention thus also relates to the quinone parent substance of ubiquinone without isoprene substituents. Ubiquinones according to the invention or derivatives thereof are also, for example, alkyl-ubiquinones, in particular 6-alkyl-ubiquinones, with preferably $C_1$–$C_{12}$-alkyl radicals. Preferred compounds are decyl-ubiquinone, in particular 6-decyl-ubiquinone, or 2,3-dimethoxy-5-methyl-6-decyl-1,4-benzoquinone.

The plastoquinones are likewise known from the literature (for example "Römpp Chemie Lexikon" [Röpp' Chemical Dictionary], Georg Thieme Verlag, Stuttgart, N.Y., 9th Edition, page 3477). They are closely related to the ubiquinones in structure and are also counted among the isoprenoid quinones, since they carry a side chain of isoprene units on the quinone ring. Preferred plastoquinones are those having 0–12, particularly preferably 1–10, and in particular 6 to 10, isoprene units in the side chain. The invention thus also relates to the quinone parent substance of plastoquinone without isoprene substituents. Plastoquinones according to the invention or derivatives thereof are, for example, also alkyl-plastoquinones with preferably $C_1$–$C_{12}$-alkyl radicals. Preferred compounds are decyl-plastoquinones, in particular 5- or 6-decyl-plastoquinone, or 2,3-dimethyl-5-decyl-1,4-benzoquinone.

During biological mitochondrial oxidation, ubiquinones function as electron transfer agents and thus play an important role in energy metabolism of animal cells. Ubiquinones have been used for a long time in cosmetic formulations as antioxidants for protection of oxidation-sensitive substances.

Plastoquinones are analogous compounds from the plant kingdom which play a role in photosynthesis in the chloroplasts of plant cells. They differ from ubiquinones in three substituents on the quinone ring, where the two methoxy groups in the ubiquinones are replaced by methyl groups and one methyl group is replaced by a hydrogen atom. However, the isoprene units bonded in the form of a chain have the same structure (cf., for example, Pfister and Arntzen, Z. f ür Naturforschung C34; 996 et seq., 1979).

The following active compounds according to the invention and combinations with these are particularly preferred:

Coenzyme Q-10, coenzyme Q-9, coenzyme Q-8, coenzyme Q-7, coenzyme Q-6, plastoquinone with 10 isoprene units (also called PQ-10, corresponding to the IUB abbreviation PQ for plastoquinones, in the formula PQ-n, n is intended to indicate the number of isoprene units (0 to 12)), PQ-9, PQ-8, PQ-7 and PQ-6.

The active compound combinations or active compounds according to the invention can be present in the topical formulations in amounts of 0.001 to 99% by weight, for example also in amounts of 0.001 to 50% by weight, in each case based on the total weight of the formulations.

The active compound combinations or active compounds according to the invention can preferably be present in the topical formulations in amounts of 0.01 to 10% by weight, in particular in amounts of 0.1 to 1% by weight, in each case based on the total weight of the formulations.

The weight ratios of the two components in the ubiquinone/plastoquinone combinations can vary within wide limits, for example in the ratio from 1:100 to 100:1, preferably in the ratio from 1:10 to 10:1. The components can also be present, for example, in the weight ratio from 1:2 to 2:1 or 1:1.

The skin care products or dermatological agents especially preferably comprise 0.2 to 0.4% by weight, in particular 0.3% by weight, of coenzyme Q-10 in combination with one or more plastoquinones or derivatives thereof.

In the context of the Application, percentages by weight based on the 100% total composition of the particular skin care preparation or dermatological agent according to the invention are always meant.

Topical formulations or compositions according to the invention with the combinations and active compounds according to the invention are all the customary use forms, for example creams (W/O, O/W or W/O/W), gels, lotions and milks.

The topical formulations according to the invention can be formulated as liquid, pasty or solid formulations, for example as aqueous or alcoholic solutions, aqueous suspensions, emulsions, ointments, creams, oils, powders or sticks. Depending on the desired formulation, the active compounds can be incorporated into pharmaceutical and cosmetic bases for topical applications which comprise, as further components, for example, oil components, fat and waxes, emulsifiers, anionic, cationic, ampholytic, zwitterionic and/or nonionic surfactants, lower mono- and polyhydric alcohols, water, preservatives, buffer substances, thickeners, fragrances, dyestuffs and opacifying agents. The active compounds according to the invention can also advantageously be used in transdermal therapeutic systems, in particular cubic systems.

It is furthermore of advantage to add to the formulations antioxidants (for example alpha-tocopherol, vitamin E and C, imidazoles, alpha-hydroxycarboxylic acids (for example malic acid, glycolic acid, gluconic acid, salicylic acid and derivatives thereof) and/or iron-complexing agents (for example EDTA or alpha-hydroxy-fatty acids) and/or known UV light protection filters, in amounts of, for example, 0.1 to 10 per cent by weight, in order to ensure the stability of the oxidation-sensitive ubiquinones or plastoquinones.

It is also advantageous to add to the formulations, in particular, 0.01–10 per cent by weight of substances or substance combinations of aerobic cell energy metabolism, for example cell energy transfer agents (such as kreatin, guanine, guanosine, adenine, adenosine, nicotine, nicotinamide or riboflavin), coenzymes (for example pantothenic acid, panthenol, liponic acid or niacin), auxiliary factors (for example L-carnitine, or uridine), substrates (for example hexoses, pentoses or fatty acids) and intermediate metabolism products (for example citric acid or pyruvate) and/or glutathione.

Formulations according to the invention can advantageously moreover comprise substances which absorb UV radiation in the UVA and/or UVB range, the total amount of filter substances being, for example, 0.1% by weight to 30% by weight, preferably 0.5 to 10% by weight, in particular 1.0 to 6.0% by weight, based on the total weight of the formulations, in order to provide cosmetic formulations which protect the skin against the entire range of ultraviolet radiation. They can also be used as sunscreen formulations for the skin. In the formulations, the UV absorbers act as antioxidants with respect to the active compounds.

If the emulsions according to the invention comprise UVB filter substances, these can be oil-soluble or water-soluble. Oil-soluble UVB filters which are advantageous according to the invention are, for example: 3-benzylidenecamphor derivatives, preferably 3-(4-methylbenzylidene)camphor and 3-benzylidenecamphor.

Advantageous water-soluble UVB filters are, for example:

salts of 2-phenylbenzimidazole-5-sulphonic acid, such as its sodium, potassium or its triethanolammonium salt, and the sulphonic acid itself.

It may also be advantageous to combine active compound combinations according to the invention with UVA filters which have usually been contained to date in cosmetic formulations. These substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione. The invention also relates to these combinations or formulations which comprise these combinations. The amounts employed for the UVB combination can be used.

The invention thus also relates to the combinations of the active compounds according to the invention, in particular in the topical formulations, with anti-oxidants, substances of aerobic cell energy metabolism and/or UV absorbers, with which, for example, the stability and the action of the formulation can be improved.

The examples mentioned above for active compounds which can be used in combinations from the active compound groups mentioned serve to describe the invention, without the intention being to limit the invention to these examples.

Protective formulation forms can furthermore be used, the substances according to the invention being enclosed (encapsulated), for example, in liposomes, micelles, nanospheres and the like of, for example, hydrogenated amphiphiles, such as, for example, ceramides, fatty acids, sphingomyelin and phosphoglycerides, or in cyclodextrans. Further protection can be achieved by the use of inert gas (for example $N_2$ or $CO_2$) during formulation and the use of gas-tight packaging forms.

Further auxiliaries and additives can be water-binding substances, thickeners, fillers, perfume, dye-stuffs, emulsifiers, active compounds such as vitamins, preservatives, water and/or salts.

During processing of the ubiquinones or plastoquinones and other oxidation-sensitive substances, the temperature should not be above 40° C. Otherwise, the usual rules, which are known to the expert, are to be observed.

The substance groups according to the invention can thus be incorporated into all cosmetic bases. In principle, however, W/O, O/W and W/O/W emulsions are preferred. Combinations according to the invention can be employed particularly advantageously in care products such as, for example, O/W creams, W/O creams, O/W lotions, W/O lotions and the like.

Unless stated otherwise, all the amounts data, percentage data or parts relate to the weight, in particular to the total weight of the formulations or of the particular mixture.

The following examples serve to describe the invention, without the intention being to limit the invention to these examples.

The parts stated are parts by weight.

EXAMPLE I

| Skin cream of the W/O type | Parts by weight |
| --- | --- |
| Vaseline DAB 9 | 13 |
| Glycerol DAB 9 | 6.3 |
| Water (CDS, completely desalinated) | 34.4 |
| Paraffin oil (mineral oil 5E, Shell) | 35 |
| Cetearyl alcohol/PEG 40-castor oil/sodium cetearyl sulphate (Emulgade F, Henkel KGaA) | 2.5 |

The aqueous phase, heated to 75° C., is added to the fat phase, heated to 75° C., and the components are stirred and homogenized until a uniformly white cream has formed. 0.03 part of plastoquinone having 9 isoprene groups (PQ-9) are dissolved in 8.5 parts of paraffin oil, the solution is added to the cream, which has cooled to about 40° C., and the components are stirred until a uniform pale yellow cream has formed.

| | Parts by weight |
| --- | --- |
| Vaseline DAB 9 | 13 |
| Glycerol DAB 9 | 6.3 |
| Water CDS | 34.67 |
| Paraffin oil (mineral oil 5E, Shell) | 43.5 |
| Cetearyl alcohol/PEG 40-castor oil/sodium cetearyl sulphate (Emulgade F, Henkel KGaA) | 2.5 |
| Plastoquinone PQ-9 | 0.03 |
| | 100 |

Example I has the following final composition:

EXAMPLE II

| Skin cream of the W/O type | Parts by weight |
| --- | --- |
| PEG 1-glyceryl oleostearate + paraffin wax | 8 |
| Vaseline DAB | 2.8 |
| Paraffin oil (mineral oil 5E, Shell) | 9.9 |
| Paraffin wax/paraffin | 1.8 |
| Ceresine | 2.2 |
| Octyldodecanol (Eutanol G, Henkel) | 10 |
| Propylene glycol | 1 |
| Glycerol | 1 |
| Magnesium sulphate | 0.7 |
| Water CDS | 59.7 |
| Total additives (perfume, preservation, stabilization) | 0.8 |

The aqueous phase, heated to 75° C., is added to the fat phase, heated to 75° C., and the components are stirred and homogenized until a uniformly white cream has formed. 0.36 part of coenzyme Q-10 and 0.04 part of plastoquinone with 9 isoprene groups, PQ-9, are dissolved in 2 parts of paraffin oil, the solution is added to the cream, which has cooled to about 40° C., and the components are stirred until a uniform pale yellow cream has formed.

Example II has the following final composition:

| | Parts by weight |
| --- | --- |
| PEG 1-glyceryl oleostearate + paraffin wax | 8 |
| Vaseline DAB | 2.8 |
| Paraffin wax/paraffin | 1.8 |
| Paraffin oil (mineral oil 5E, Shell) | 11.9 |
| Ceresine | 2.2 |
| Octyldodecanol | 10 |
| Plastoquinone, PQ-9 | 0.04 |
| Coenzyme Q-10 | 0.36 |
| Propylene glycol | 1 |
| Glycerol | 1 |
| Magnesium sulphate | 0.7 |
| Water CDS | 59.4 |
| Total additives (perfume, preservation, stabilization) | 0.8 |
| | 100 |

EXAMPLE III

| Skin cream of the O/W type | Parts by weight |
| --- | --- |
| Octyldodecanol | 9.3 |
| (Eutanol G, Henkel KGaA) | |
| Cetearyl alcohol/PEG 40- | 3.7 |
| castor oil/sodium cetearyl | |
| sulphate (Emulgade F, Henkel KGaA) | |
| Water CDS | 73.7 |
| Glycerol DAB 9 | 4.6 |
| Paraffin oil | 5.8 |
| (mineral oil 5E, Shell) | |

The aqueous phase, heated to 75° C., is added to the fat phase, heated to 75° C., and the components are stirred and homogenized until a uniformly white cream has formed. 0.54 part of coenzyme Q-10 and 0.35 part of coenzyme Q-6 and 0.01 part by weight of plastoquinone PQ-9 are dissolved in 2 parts of paraffin oil, the solution is added to the cream, which has cooled to about 40° C., and the components are stirred until a uniform pale yellow cream has formed.

Example III has the following final composition:

| | Parts by weight |
| --- | --- |
| Octyldodecanol | 9.3 |
| (Eutanol G, Henkel KGaA) | |
| Cetearyl alcohol/PEG 40- | 3.7 |
| castor oil/sodium cetearyl | |
| sulphate (Emulgade F, Henkel KGaA) | |
| Water CDS | 73.7 |
| Glycerol DAB 9 | 4.6 |
| Paraffin oil | 7.8 |
| (mineral oil 5E, Shell) | |
| Plastoquinone PQ-9 | 0.01 |
| Coenzyme Q-6 | 0.35 |
| Coenzyme Q-10 | 0.54 |
| | 100 |

EXAMPLE IV

| O/W lotion | Parts by weight |
| --- | --- |
| Steareth-2 | 3 |
| Steareth-21 | 2 |
| Cetearyl alcohol/PEG 40- | 2.5 |
| castor oil/sodium cetearyl | |
| sulphate (Emulgade F, Henkel KGaA) | |
| Paraffin oil | 10.1 |
| (mineral oil 5E, Shell) | |
| Propylene glycol | 1 |
| Glycerol | 1 |
| Water CDS | 74.3 |
| Total additives (perfume, preservation, stabilization) | 0.8 |

The aqueous phase, heated to 75° C., is added to the fat phase, heated to 75° C., and the components are stirred and homogenized until a uniformly white lotion has formed. 0.2 part of coenzyme Q-10 and 0.2 part of plastoquinone PQ-9 are dissolved in 4 parts of paraffin oil, the solution is added to the lotion, which has cooled to about 40° C., and the components are stirred until a uniform pale yellow lotion has formed.

Example IV has the following final composition:

| | Parts by weight |
| --- | --- |
| Steareth-2 | 3 |
| Steareth-21 | 2 |
| Cetearyl alcohol/PEG 40- | 2.5 |
| castor oil/sodium cetearyl | |
| sulphate (Emulgade F, Henkel KGaA) | |
| Paraffin oil | 14.1 |
| (mineral oil 5E, Shell) | |
| Propylene glycol | 1 |
| Coenzyme Q-6 | 0.2 |
| Plastoquinone PQ-9 | 0.2 |
| Glycerol | 1 |
| Water CDS | 74.3 |
| Total additives (perfume, preservation, stabilization) | 0.8 |
| | 100 |

EXAMPLE V

| O/W lotion | Parts by weight |
| --- | --- |
| Octyldodecanol | 5.6 |
| (Eutanol G, Henkel KGaA) | |
| Cetearyl alcohol/PEG 40- | 8.9 |
| castor oil/sodium cetearyl | |
| sulphate (Emulgade F, Henkel KGaA) | |
| Cetearyl isononanoate | 7.5 |
| (Cetiol 5N, Henkel KGaA) | |
| Water CDS | 62.3 |
| Glycerol DAB 9 | 4.7 |
| Paraffin oil | 5.7 |
| (mineral oil 5E, Shell) | |

The aqueous phase, heated to 75° C., is added to the fat phase, heated to 75° C., and the components are stirred and homogenized until a uniformly white cream has formed. 0.04 part of coenzyme Q-10 and 0.36 part of plastoquinone PQ-9 are dissolved in 5 parts of paraffin oil, the solution is added to the cream, which has cooled to about 40° C., and the components are stirred until a uniform pale yellow cream has formed.

Example V has the following final composition:

| | Parts by weight |
| --- | --- |
| Octyldodecanol | 5.6 |
| (Eutanol G, Henkel KGaA) | |
| Cetearyl alcohol/PEG 40- | 8.9 |
| castor oil/sodium cetearyl | |
| sulphate (Emulgade F, Henkel KGaA) | |
| Cetearyl isoflonanoate | 7.5 |
| (Cetiol 5N, Henkel KGaA) | |
| Water CDS | 62.3 |
| Glycerol DAB 9 | 4.7 |
| Paraffin oil | 10.7 |
| (mineral oil 5E, Shell) | |
| Coenzyme Q-10 | 0.04 |
| Plastoquinone PQ-9 | 0.36 |
| | 100 |

EXAMPLE VI

| Skin oil | Parts by weight |
| --- | --- |
| Glyceryl tricaprylate (Miglyol 812, Dynamit Nobel) | 22.7 |
| Hexyl laurate (Cetiol A, Henkel KGaA) | 22 |
| Octyl stearate (Cetiol 886, Henkel KGaA) | 20 |
| Paraffin oil (mineral oil SE, Shell) | 35 |
| Plastoquinone PQ-9 | 0.1 |
| Coenzyme Q-6 | 0.2 |
|  | 100 |

The components are stirred at 25° C. until a uniform, clear mixture has formed.

EXAMPLE VII

| Skin oil | Parts by weight |
| --- | --- |
| Glyceryl tricaprylate (Miglyol 812, Dynamit Nobel) | 21 |
| Hexyl laurate (Cetiol A, Henkel KGaA) | 20 |
| Octyl stearate (Cetiol 886, Henkel KGaA) | 21.7 |
| Paraffin oil (mineral oil 5E, Shell) | 37 |
| Plastoquinone PQ-9 | 0.3 |
|  | 100 |

EXAMPLE VIII

| Skin cream of the W/O type | Parts by weight |
| --- | --- |
| Vaseline DAB 9 | 13 |
| Glycerol DAB 9 | 6.3 |
| Water CDS | 34.4 |
| Paraffin oil (mineral oil 5E, Shell) | 35 |
| Cetearyl alcohol/PEG 40-castor oil/sodium cetearyl sulphate (Emulgade F, Henkel KGaA) | 2.5 |

The aqueous phase, heated to 75° C., is added to the fat phase, heated to 75° C., and the components are stirred and homogenized until a uniformly white cream has formed. 0.27 part of coenzyme Q-10 and 0.03 part by weight of plastoquinone PQ-6 are dissolved in 8.5 parts of paraffin oil, the solution is added to the cream, which has cooled to about 40° C., and the components are stirred until a uniform pale yellow cream has formed.

Example VIII has the following final composition:

|  | Parts by weight |
| --- | --- |
| Vaseline DAB 9 | 13 |
| Glycerol DAB 9 | 6.3 |
| Water CDS | 34.4 |
| Paraffin oil (mineral oil 5E, Shell) | 43.5 |
| Cetearyl alcohol/PEG 40-castor oil/sodium cetearyl sulphate (Emulgade F, Henkel KGaA) | 2.5 |
| Plastoquinone, 6 isoprene units | 0.03 |
| Coenzyme Q-10 | 0.27 |
|  | 100 |

We claim:

1. Topical formulations useful in the treatment of aging skin comprising one or more compounds selected from the group consisting of ubiquinones and derivatives thereof together with one or more compounds selected from the group consisting of plastoquinones and derivatives thereof.

2. Formulations according to claim 1, wherein the ubiquinones or plastoquinones have 0 to 12 isoprene units, alkyl radicals or both.

3. Formulations according to claim 1, wherein the ubiquinones or plastoquinones have 9 or 10 isoprene units.

4. Formulations according to claim 1, further comprising antioxidants, substances of aerobic cell energy metabolism, UV absorbers or combinations thereof.

5. Formulations according to claim 1, which are cosmetic or dermatological formulations in the form of W/O, O/W or W/O/W emulsions.

6. A method for the prophylaxis or treatment of chronological aging of the skin or the aging of the skin of exogenous origin which comprises applying to said skin an effective amount of at least one plastoquinone or a derivative thereof optionally in combination with at least one ubiquinone or derivative thereof.

* * * * *